United States Patent [19]

Bungard et al.

[11] 4,234,687
[45] Nov. 18, 1980

[54] β-GALACTOSIDASE

[75] Inventors: Stephen J. Bungard; David Byrom, both of Stockton-on-Tees, England

[73] Assignee: Imperial Chemical Industries Limited, London, England

[21] Appl. No.: 831,914

[22] Filed: Sep. 9, 1977

[30] Foreign Application Priority Data

Sep. 19, 1976 [GB] United Kingdom ............... 38002/76

[51] Int. Cl.$^3$ ........................ C12P 19/14; C12N 9/38; C12R 1/01
[52] U.S. Cl. ....................................... 435/99; 435/207; 435/822
[58] Field of Search ................. 195/62, 66 R, 65, 3 R; 435/99, 207, 822

[56] References Cited

U.S. PATENT DOCUMENTS

| 3,919,049 | 11/1975 | Kiuchi et al. | 195/66 R |
| 3,981,773 | 9/1976 | Galzy et al. | 195/31 R |
| 4,007,283 | 2/1977 | Crisan et al. | 195/31 R |

Primary Examiner—Thomas G. Wiseman
Attorney, Agent, or Firm—Cushman, Darby & Cushman

[57] ABSTRACT

A process for producing the enzyme β-galactosidase (lactase) involving a novel microorganism (NCIB No 11259) of unknown genus and for using the enzyme to hydrolyse lactose to glucose and galactose.

16 Claims, No Drawings

β-GALACTOSIDASE

THIS INVENTION RELATES to a β-galactosidase (lactase) enzyme, an enzyme preparation containing β-galactosidase, a method for producing the enzyme or preparation, a method for the hydrolysis of lactose using the enzyme or preparation and to novel microorganisms capable of producing the enzyme or preparation.

β-galactosidase or lactase is an enzyme capable of hydrolysing lactose to produce a mixture of galactose and glucose which may be concentrated into a syrup. Lactose is usually regarded as a waste product and has a very limited market. By treatment with β-galactosidase lactose can be converted into a useful product.

Most β-galactosidase enzymes are inhibited by calcium ions and many are not stable at higher temperatures, i.e. temperatures of 50° C. or more.

According to the present invention we provide a β-galactosidase enzyme or an enzyme preparation containing β-galactosidase prepared by culturing a microorganism, belonging to the genus of which the microorganism LT-2 (NCIB No: 11259) (whose characteristics are hereinafter described) is a member, and capable of producing the enzyme or preparation, in a medium containing appropriate nutrients.

Further according to the invention we provide a method for hydrolysing lactose to produce a mixture containing galactose and glucose using a β-galactosidase enzyme or an enzyme preparation containing β-galactosidase wherein the enzyme or preparation is produced by culturing a microorganism, belonging to the genus of which the microorganism LT-2 (NCIB No: 11259) (whose characteristics are hereinafter described) is a member, and capable of producing the enzyme or preparation, in a medium containing appropriate nutrients.

Further according to the invention we provide microorganisms capable of producing a β-galactosidase enzyme which belong to the species of which the microorganism LT-2 (NCIB No: 11259) (whose characteristics are hereinafter described) is a member, said species being referred to hereinafter as the LT-2 species.

Further according to the invention we provide a method for producing a β-galactosidase enzyme or an enzyme preparation containing β-galactosidase wherein a microorganism, belonging to the genus of which the microorganism LT-2 (NCIB No: 11259) (whose characteristics are hereinafter described) is a member, and capable of producing the enzyme or preparation, is cultured in a medium containing appropriate nutrients.

The microorganism LT-2 is a gram-positive rod which is not coryneform and has the properties listed in Table 1. Of well accepted genera into which it might be classified the closest are Bacillus, Kurthia and Lactobacillus. However LT-2 has important differences from the described properties of these genera, e.g. absence of spores, different GC content, that LT-2 belongs to a novel genus which will be referred to hereinafter as the LT-2 genus.

β-galactosidase-producing members of the LT-2 species, especially strain LT-2 itself, are very suitable for producing the enzyme or enzyme preparation of the invention and in the method of the invention for hydrolysing lactose.

A culture of the novel strain LT-2 has been deposited at the National Collection of Industrial Bacteria (NCIB), Torry Research Station, Aberdeen, Scotland, UK and has been given the NCIB Accession No: 11259.

The microbiological characteristics of strain LT-2 as determined by standard microbiological tests are given in Table 1.

TABLE 1

| Characteristic Test | | Property of LT-2 |
|---|---|---|
| Colony Description (Basal salts + 0.1% yeast extract + 0.5% peptone + 1.5% Oxoid purified agar) 50° C. 18 h | | 1-2 mm. Circular, irregular edge convex rough/wrinkled surface, cream, dense, easily dispersed. |
| Gram Stain (Medium as above) 50° 18 h | | Medium to long, pleomorphic rods. Slender/stout. Some slightly curved. Gram +ve/−ve. Some cells partly +ve, partly −ve, including some with +ve ends. Single cells and clusters. Some chains, often with a mixture of the +ve and −ve cells in a single chain. Cells have parallel sides, straight axes and rounded ends. |
| *Motility | | − |
| Anaerobic growth | | + |
| Gelatin hydrolysis (plate) | | weak + (3 days) |
| Litmus milk | | acid + clot (3 days) |
| Starch hydrolysis | | − |
| $NO_3^-$ to $NO_2^-$ | | − |
| Oxidase | | − |
| *Catalase | | + |
| Lecithinase (egg yolk plate) | | − (growth +) |
| *MR | | + |
| *VP | | − |
| Indole | | − |
| Cellulose hydrolysis | | − |
| *Phenylalanine deamination | | − |
| *Arabinose[a] | acid | − |
|  | gas | − |
| *Mannitol[a] | acid | − |
|  | gas | − |
| *Xylose[a] | acid | − |
|  | gas | − |
| *Glucose[a] | acid | + |
|  | gas | − |
| Growth At | 55° C. | + |

TABLE 1-continued

| Characteristic Test | | Property of LT-2 |
|---|---|---|
| | 23° C. | + |
| | 4° C. | − |
| *Growth In | 5% NaCl | − |
| * | 7% NaCl | − |
| * | 10% NaCl | − |
| * | 0.001% lysozyme | − |
| * | Sabouraud dextrose agar | + |
| | Sabouraud dextrose broth | + |
| G + C Content-51.7 moles % | | |
| Pathogenicity | | Non pathogenic |
| Koser's Citrate | | − |
| Arginine Dihydrolase | | − |
| Mollars | | |
| Growth at pH 8.5 | | + |
| Growth at pH 9.5 | | − |

*These tests were performed with cultures grown at both 37° C. and 50° C. All other tests were performed with cells grown at 50° C. only. The only difference observed between cultures grown at the two temperatures was thicker growth in 7% NaCl at 37° C.
<sup>a</sup>Peptone water sugar, Andrade's indicator.

Other strains which are very suitable for use in the present invention include β-galactosidase producing variants and mutants of strains LT-2.

In the method for producing β-galactosidase or an enzyme preparation containing β-galactosidase, the β-galactosidase producing microorganism is grown in a culture medium containing a suitable carbon source and other appropriate nutrients thus forming the enzyme. Growth may be in batch or continuous culture. For example an inoculum containing a β-galactosidase producing strain is prepared, e.g. on an agar slant, and is used to inoculate a suitable culture medium. Here the microorganism is allowed to grow and to produce β-galactosidase. The incubation period may vary over a wide range depending upon the particular microorganism used and upon the culture medium; preferably it is between 4 and 48 hours. An aliquot or the entire culture is then used to inoculate a larger volume of nutrient. This may be repeated one or more times.

Microbial cells containing the enzyme may be separated from the final culture medium by any known means. Preferably the whole cells are used to carry out the hydrolysis of lactose. However, if desired the enzyme may be extracted from the cells by any suitable method or the final culture medium itself may be used, without separating the cells, in the hydrolysis of lactose.

The culture medium for the production of the enzyme or enzyme preparation preferably contains as the carbon source a suitable carbohydrate, e.g lactose or galactose. It may also contain complex organic nutrients such as a vitamin rich broth comprising yeast extract, meat extract etc. The nitrogen source is suitably ammonia, a nitrate or an amino acid and the phosphorus source suitably a phosphate. Other elements present preferably include magnesium, potassium and sulphur, e.g added as magnesium sulphate and potassium sulphate and trace elements such as iron, cobalt, zinc, copper, manganese, calcium etc.

The preferred proportions in which the various nutrients are present in the culture medium for production of the enzyme will vary to some extent depending upon the microorganism employed and other factors. Suitable proportions in any particular instance may be determined readily by a competent microbiologist.

During production of β-galactosidase the culture medium is preferably maintained at a temperature in the range 30° to 60°, especially 45° to 55° C. Preferably the pH of the medium is maintained in the range 4.5 to 8.0, especially 6.5 to 7.0.

The hydrolysis of lactose to glucose and galactose can go essentially to completion to give a 1:1 mixture of glucose and galactose. Under optimum conditions for an industrial process the reaction is not allowed to go to completion and the product is a syrup containing lactose, glucose and galactose. During the hydrolysis the temperature is suitably maintained in the range 20° to 70° C., preferably 40° to 60° C., temperatures of about 50° C. being especially preferred. The pH of the lactose-containing medium undergoing hydrolysis is preferably maintained in the range 4.0 to 8.0, especially 6.0 to 7.5, if necessary using a suitable buffer system, e.g phosphate buffer. However, in large scale processes buffering is to be avoided if possible. Very suitably the enzyme or enzyme preparation may be immobilised and used as part of a continuous column process, e.g using the process of B.P No. 1 368 650.

The lactose itself may be present in the medium for the hydrolysis process in amounts in the range 5 to 40% by weight. It can be present wholly or partially in whey or milk both of which contain lactose. For the hydrolysis of lactose the enzyme may be present in whole cells or in soluble form, the microorganism cells having been split open and debris such as cell walls separated.

The β-galactosidases produced according to the invention, particularly that from strain LT-2, have advantages in that they are not inhibited by calcium ions and are stable at temperatures such as 50° C. Thus the hydrolysis process can be run at temperatures such as 50° C. at which higher temperatures contamination with unwanted microorganisms is greatly reduced.

The syrup produced by the hydrolysis process may be used as a sweetener generally. It is also very useful in brewing as a substitute for glucose.

The β-galactosidase of the invention may be assayed for its lactose-hydrolysing activity by the following assay method:

β-GALACTOSIDASE-ASSAY METHOD

An assay of the activity of the lactose-hydrolysing enzyme was performed in the following reaction mixtures:

| | |
|---|---|
| 0.05 M phosphate buffer pH 6.5 | 0.5 ml |
| 4.7% (<sup>w</sup>/v) KF | 0.5 ml |
| 5.0% (<sup>w</sup>/v) Lactose | 5.0 ml |

| | |
|---|---|
| -continued | |
| Bacterial culture (toluenised for 10mmin) or enzyme solution | 1.0 ml |

The reaction mixture was incubated at 50° C. for ten minutes. The reaction was started by the addition of the lactose and stopped by the addition of 5 ml of 10% (w/v) trichloracetic acid. Glucose was determined by the use of a Beckman Glucose Analyser. A control assay was performed to the reaction mixture.

The amount of enzyme necessary to produce 1 mg of glucose per hour at 50° C. under the above assay conditions was defined as one unit of enzyme.

Activity levels in excess of 60 units per ml of culture have been routinely observed in samples from continuous cultures of LT-2.

This invention is illustrated by the following Examples:

EXAMPLE 1

Lactose was produced by culturing the microorganism LT-2 in continuous culture at a dilution rate of 0.2 $h^{-1}$, in a medium with the following composition:

| | |
|---|---|
| $MgSO_4$ | 1.2 g/l |
| $K_2SO_4$ | 0.45 g/l |
| $NaSO_4$ | 0.1 g/l |
| Bacto-Peptone | 3.0 g/l |
| "Difco" Yeast Extract | 1.0 g/l |
| Lactose | 20 g/l |
| 1.1 M Phosphoric acid | 24 ml/l |
| Trace Elements Solution | 24 ml/l |

The Trace Elements Solution had the following composition:

| | |
|---|---|
| $FeSO_4 . 7 H_2O$ | 0.50 g/l |
| $CuSO_4 . 5 H_2O$ | 0.01 g/l |
| $MnSO_4 . 4 H_2O$ | 0.05 g/l |
| $ZnSO_4 . 7 H_2O$ | 0.05 g/l |
| $CaCl_2 . H_2O$ | 1.32 g/l |
| $CoCl_2 . H_2O$ | 0.01 g/l |
| $H_3BO_3$ | 0.007 g/l |
| $Na_2MoO_4$ | 0.01 g/l |
| Conc $H_2SO_4$ | 0.3 ml/l |

The pH of the culture was maintained at 6.8 by the controlled addition of ammonia.

A dry cell weight of 9 to 10 g/l and a β-galactosidase activity of 50 to 70 units/ml were maintained for over 5 weeks.

EXAMPLE 2

A sample from the culture described in Example 1 was processed according to the method of BP No. 1 368 650 to produce pellets containing β-galactosidase activity.

5 g of these pellets were swollen in 0.05 M phosphate buffer pH 6.5 for 20 min, and placed in a jacketed column kept at 50° C. A 5% (w/v) lactose solution was passed through the column at 50° C., pH 6.5 and 50 ml/h. Initially 65% hydrolysis of the lactose was brought about by this mode of operation.

We claim:

1. A method for producing a composition selected from the group consisting of β-galactosidase enzyme and enzyme preparations containing β-galactosidase, comprising:
    culturing a microorganism having the identifying characteristics of the microorganism LT-2 (NCIB No: 11259) capable of producing β-galactosidase, in a medium containing appropriate nutrients, and recovering the β-galactosidase.

2. A method according to claim 1 wherein the microorganism is LT-2 (NCIB No: 11259).

3. A method according to claim 2 wherein the medium contains as a carbon source a carbohydrate selected from the group consisting of lactose and galactose.

4. A method according to claim 2 wherein the medium contains as a nitrogen source a compound selected from the group consisting of ammonia, nitrates and amino acids.

5. A method according to claim 2 wherein the medium contains sources of carbon, nitrogen, phosphorus, magnesium, potassium and sulphur.

6. A method according to claim 2 wherein the medium is maintained at a temperature in the range 30° to 60° C.

7. A method according to claim 2 wherein the medium is maintained at a pH in the range 4.5 to 8.0.

8. A method according to claim 1 wherein the medium contains as a carbon source a carbohydrate selected from the group consisting of lactose and galactose.

9. A method according to claim 1 wherein the medium contains as a nitrogen source a compound selected from the group consisting of ammonia, nitrates and amino acids.

10. A method according to claim 1 wherein the medium contains sources of carbon, nitrogen, phosphorus, magnesium, potassium and sulphur.

11. A method according to claim 1 wherein the medium is maintained at a temperature in the range 30° to 60° C.

12. A method according to claim 1 wherein the medium is maintained at a pH in the range 4.5 to 8.0.

13. A method of hydrolysing lactose to produce a mixture containing galactose and glucose, comprising:
    hydrolysing lactose with a microorganism having the identifying characteristics of the microorganism LT-2 (NCIB No: 11259) capable of producing β-galactosidase enzyme.

14. A method according to claim 8 wherein the microorganism is LT-2 (NCIB No: 11259).

15. A method according to claim 13 wherein during the hydrolysis the temperature is maintained in the range 20° to 70° C.

16. A method according to claim 13 wherein during the hydrolysis the pH is maintained in the range 4.0 to 8.0.

* * * * *